United States Patent
Kakoti

(10) Patent No.: US 12,272,026 B2
(45) Date of Patent: Apr. 8, 2025

(54) ENHANCED DIGITAL PATHOLOGY PLATFORM

(71) Applicant: Gestalt Diagnostics, LLC, Spokane, WA (US)

(72) Inventor: Roopam Kakoti, Spokane, WA (US)

(73) Assignee: Gestalt Diagnostics, LLC, Spokane, WA (US)

( * ) Notice: Subject to any disclaimer, the term of this patent is extended or adjusted under 35 U.S.C. 154(b) by 414 days.

(21) Appl. No.: 17/741,302

(22) Filed: May 10, 2022

(65) Prior Publication Data

US 2023/0368346 A1 Nov. 16, 2023

(51) Int. Cl.
| | |
|---|---|
| G06T 7/00 | (2017.01) |
| G06T 5/50 | (2006.01) |
| G06T 7/90 | (2017.01) |
| G06T 11/00 | (2006.01) |
| G06T 11/20 | (2006.01) |
| G16H 30/40 | (2018.01) |

(52) U.S. Cl.
CPC .............. G06T 5/50 (2013.01); G06T 7/0012 (2013.01); G06T 7/90 (2017.01); G06T 11/001 (2013.01); G06T 11/203 (2013.01); G16H 30/40 (2018.01); G06T 2200/24 (2013.01); G06T 2207/10024 (2013.01); G06T 2207/20092 (2013.01); G06T 2207/20221 (2013.01); G06T 2207/30004 (2013.01)

(58) Field of Classification Search
CPC .......... G06T 7/00; G06T 7/0012; G06T 5/50; G06T 11/00; G06T 11/20; G06T 11/001; G06T 11/203; G06T 7/90; G06T 2200/24; G06T 2207/10024; G06T 2207/20221; G06T 2207/20092; G16H 30/40
See application file for complete search history.

(56) References Cited

U.S. PATENT DOCUMENTS

| | | | |
|---|---|---|---|
| 2019/0355113 A1* | 11/2019 | Wirch | ..................... G06T 7/136 |
| 2020/0294231 A1 | 9/2020 | Tosun et al. | |
| 2020/0334814 A1 | 10/2020 | Gholap | |

FOREIGN PATENT DOCUMENTS

| | | |
|---|---|---|
| EP | 3862917 A1 | 8/2021 |
| WO | 2022232078 A1 | 11/2022 |

OTHER PUBLICATIONS

The Extended European Search Report and Written Opinion mailed Sep. 11, 2023 for European patent application No. 23171434.6, 12 pages.
Search Report mailed Nov. 10, 2023 for Great Britain Application No. GB2306821.6, a foreign counterpart to U.S. Appl. No. 17/741,302, 1 page.

* cited by examiner

*Primary Examiner* — Tuan H Nguyen
(74) *Attorney, Agent, or Firm* — Lee & Hayes, P.C.

(57) ABSTRACT

Techniques may include enhanced digital pathology platforms. Image data representing a whole slide image (WSI) may be obtained for medical testing or medical evaluation. One or more algorithms may be determined based at least in part on the image data for the WSI based on a set of rules. The one or more algorithms may be executed to obtain one or more results associated with the WSI. The one or more results may be integrated to generate a combined image. The combined image may be displayed via a user interface of a digital pathology platform.

18 Claims, 15 Drawing Sheets

| | VENDORS | ALGORITHMS | VERSIONS | SLIDE IDs | STATUS |
|---|---|---|---|---|---|
| 612 | VENDOR 2 | BREAST BIOM | 1.0 | A1-IMH-2 | ☒ |
| 614 | VENDOR 1 | BREAST BIOM | 1.0 | A1-IMH-1 | ☒ |
| 616 | VENDOR 2 | MITOTIC # | 2.0 | A1-IMH-1 | ☒ |
| 618 | VENDOR 2 | BREAST BIOM | 1.0 | A1-IMH-2 | ☒ |
| 620 | VENDOR 1 | BREAST BIOM | 2.0 | A1-IMH-2 | ☒ |
| 622 | VENDOR 2 | MITOTIC # | 1.0 | A1-IMH-2 | ☒ |
| 624 | VENDOR 3 | MITOTIC # | 2.0 | A1-IMH-3 | ☒ |
| 626 | VENDOR 2 | MITOTIC # |  | A1-IMH-4 | ... |

PRESENT A GRAPHICAL ELEMENT TO SELECTIVELY DISPLAY THE FIRST RESULT VIA THE USER INTERFACE OF THE DIGITAL PATHOLOGY PLATFORM
824

RECEIVE AN INDICATION OF A SELECTION OF THE GRAPHICAL ELEMENT
826

BASED AT LEAST IN PART ON THE INDICATION, PERFORM AT LEAST ONE OF SHOWING OR HIDING THE FIRST RESULT IN THE COMBINED IMAGE VIA THE USER INTERFACE OF THE DIGITAL PATHOLOGY PLATFORM
828

FIG. 8E

ENHANCED DIGITAL PATHOLOGY PLATFORM

BACKGROUND

Whole slide imaging, which refers to scanning conventional glass slides and creating a high-resolution digital image thereof, is a significant technologic development being employed by pathology departments worldwide. Pathologists may work on whole slide images (WSIs) via a digital pathology platform, which is a dynamic, image-based environment that enables pathologists to review, manage, and analyze the digital slides. However, since pathologists work on a great number of digital slides on a daily basis, performing image analysis on each slide image on the digital pathology platform may be burdensome and time-consuming.

BRIEF DESCRIPTION OF THE DRAWINGS

The Detailed Description is set forth with reference to the accompanying figures. The use of the same reference numbers in different figures indicates similar or identical items. The detailed description is set forth with reference to the accompanying figures. In the figures, the left-most digit(s) of a reference number identifies the figure in which the reference number first appears. The use of the same reference numbers in different figures indicates similar or identical items or features. Furthermore, the drawings may be considered as providing an approximate depiction of the relative sizes of the individual applications within individual figures. However, the drawings are not to scale, and the relative sizes of the individual applications, both within individual figures and between the different figures, may vary from what is depicted. In particular, some of the figures may depict applications in a certain size or shape, while other figures may depict the same applications on a larger scale or differently shaped for the sake of clarity.

FIG. 6 is an example table showing the corresponding relationship of vendors, algorithms, versions, slide IDs, and status according to implementations of this disclosure.

FIG. 8A, FIG. 8B, FIG. 8C, FIG. 8D, and FIG. 8E illustrate an example process for enhancing the digital pathology platform according to implementations of this disclosure.

DETAILED DESCRIPTION

Figure 1A:
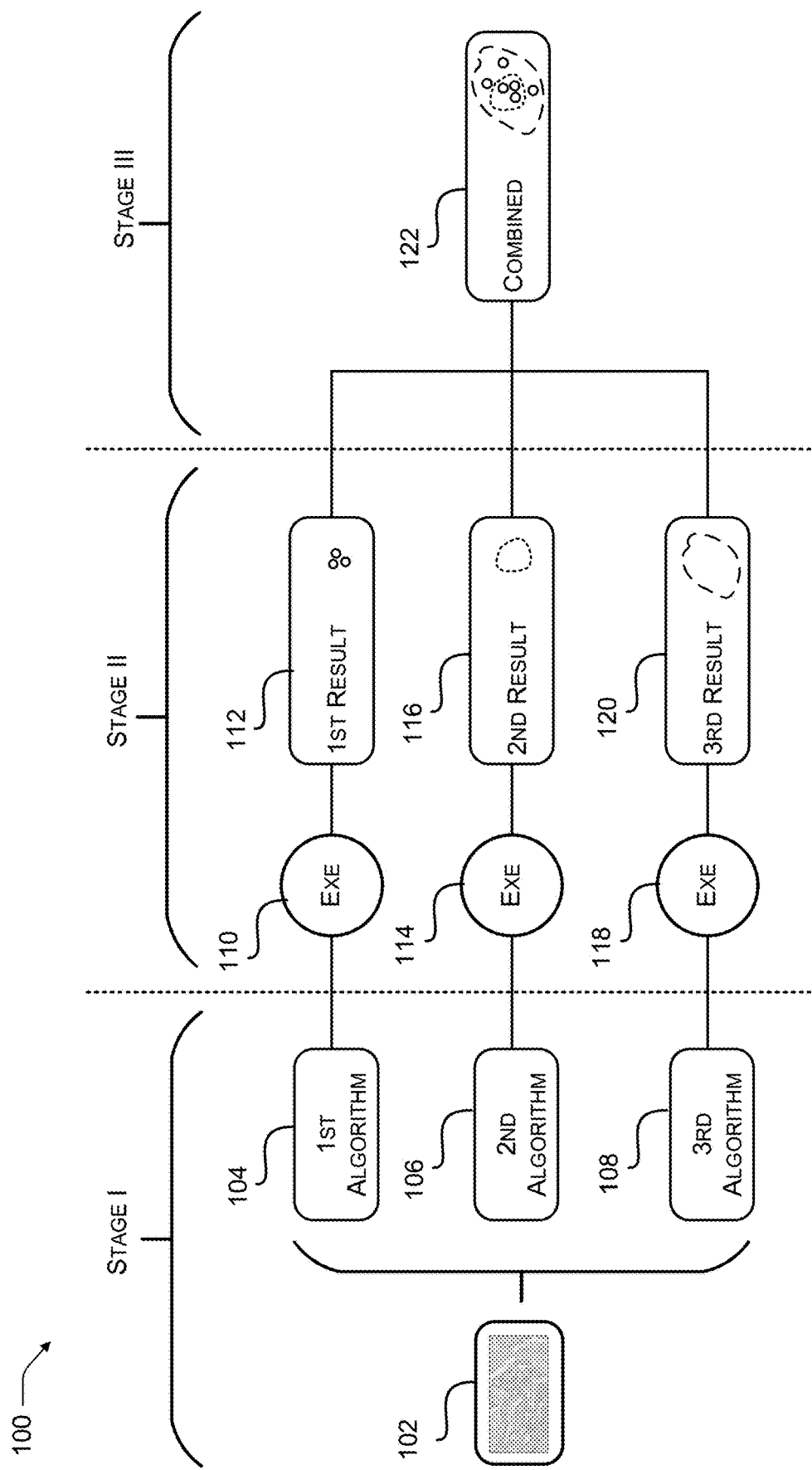
FIG. 1A is an example schematic diagram showing a process for performing image analysis on a WSI according to implementations of this disclosure.

This disclosure is generally directed to digital pathology. More particularly, this disclosure is directed to methods, apparatuses, and computer-readable media for enhancing image analysis.

In various implementations, image data representing a whole slide image (WSI) may be obtained for medical testing or medical evaluation. One or more algorithms may be determined based at least in part on the image data for the WSI based on a set of rules. The one or more algorithms may be executed to obtain one or more results associated with the WSI. The one or more results may be integrated to generate a combined image. The combined image may be displayed via a user interface of a digital pathology platform.

In implementations, the set of rules includes at least one of specimen type associated with the WSI, a stain type associated with the WSI, and/or a procedure code associated with the WSI. In implementations, the rules may be set regarding how to assign various algorithms to various WSIs based on parameters such as the specimen type, the stain type, the procedure code, and so on. In practice, the user may view, edit, add, and/or delete the rules via the user interface of the digital pathology platform.

In implementations, the corresponding relationship of vendors, algorithms, versions, slide IDs, and status may be saved in a table or other data structure. The table may be maintained by the digital pathology platform. The user may review the corresponding relationship of vendors, algorithms, versions, slide IDs, and status on the digital pathology platform conveniently.

In implementations, the corresponding relationship between the specimen type, the vendor, and the algorithm may be presented via the user interface of the digital pathology platform.

In implementations, the one or more algorithms may include at least two algorithms. The at least two algorithms may be executed in parallel. Additionally or alternatively, at least two algorithms may be executed sequentially. In implementations, the one or more algorithms may be executed on different platforms. In implementations, the one or more algorithms may be executed at different places. In some examples, the at least two algorithms may be executed on the same computing device.

In implementations, the one or more results include different types of results such as biomarker, cell segmentation, mitotic count, tissue boundary and patterns, and so on.

In implementations, the one or more algorithms may comprise a first algorithm and a second algorithm. The techniques may further comprise executing the first algorithm on a first computing device, and executing the second algorithm on a second computing device that is different than the first computing device.

In implementations, the one or more results may comprise a first result and a second result. In some examples, the techniques may further comprise representing the first result in the combined image with a first line type, and representing the second result in the combined image with a second line type. In some examples, the techniques may further comprise representing the first result in the combined image with a first color, and representing the second result in the combined image with a second color. In implementations, the first result and the second result may be presented in an overlapping manner.

In implementations, a graphical element may be presented to selectively display the first result via the user interface of the digital pathology platform. An indication of a section of the graphical element may be received. based at least in part on the indication, at least one of showing or hiding the first result in a combined image via the user interface of the digital pathology platform.

In terms of configurability, the display of results of Image Analysis (IA) algorithms may be enabled/disabled by the user. Moreover, the execution of algorithms is configurable by enabling or disabling the algorithms. The rules of selecting/assigning algorithms may be changed/edited conveniently via the user interface of the digital pathology platform. In terms of extensibility, new algorithms may be added to be executed at any time, and existing algorithms may be removed to be executed at any time. Results generated by new algorithms may be added to the WSI via the user interface of the digital pathology platform at any time, and results generated by existing algorithms may be removed from the WSI via the user interface of the digital pathology platform at any time. Moreover, additional rules for selecting/assigning algorithms may be added based on needs.

With the techniques described herein, algorithms may be assigned to the WSI automatically based on a set of rules, and simultaneous execution of multi-vendors multi-algorithms image analysis on WSIs can be achieved. Various results can be integrated into a combined image to be displayed via the user interface on the digital pathology platform. The user may view the combined image with multi-vendors multi-algorithms results conveniently and control the results to be shown/hidden in the combined image. Moreover, the user may view and edit the rules regarding which algorithm is assigned to which type of specimen via the user interface on the digital pathology platform. Thus, the usability of the digital pathology platform can be improved, thereby improving the functionality of computing devices.

FIG. 1A is an example schematic diagram showing a process 100 for performing image analysis on a WSI 102 according to implementations of this disclosure. In implementations, the WSI 102 may be a digital slide obtained by scanning of conventional glass slides, and include information/data regarding a specimen.

Referring to FIG. 1A, in stage I, various algorithms from various vendors may be assigned to the WSI 102. For example, a first algorithm 104, a second algorithm 106, and a third algorithm 108 are assigned to the WSI 102. Though three algorithms are shown in FIG. 1A, there may be other numbers of algorithms assigned to the WSI 102. In implementations, the first algorithm 104, the second algorithm 106, and the third algorithm 108 may be provided by the same vendor (or organization or entity) or different vendors. As an example, the first algorithm 104 is provided by a first vendor, the second algorithm 106 is provided by a second vendor, and the third algorithm 108 is provided by a third vendor. As another example, the first algorithm 104, the second algorithm 106, and the third algorithm 108 are provided by the same vendor. In implementations, the algorithms can represent machine learned models trained to perform particular functions, such as identifying tissue types, identifying abnormal cells (e.g., cancer cells), labeling cells, classifying and/or segmenting cells, etc. In implementations, access to the various algorithms may be determined via licensing and security. In implementations, the digital pathology platform may assign various algorithms to various WSIs based on a set of rules automatically. Additional details are given throughout this disclosure.

In stage II, various algorithms are executed to generate various results associated with the WSI 102. In implementations, the various algorithms may be executed in parallel. Additionally or alternatively, the various algorithms may be executed sequentially. In implementations, new algorithms may be added to the execution path at any time, and existing algorithms may be removed from the execution path at any time. Moreover, the execution of algorithms is configurable by enabling or disabling the algorithms. In implementations, the various results associated with the WSI 102 may include various types of results.

At 110, the first algorithm 104 is executed. At 112, a first result associated with the WSI 102 is generated by executing the first algorithm 104. At 114, the second algorithm 106 is executed. At 116, a second result associated with the WSI 102 is generated by executing the second algorithm 106. At 118, the third algorithm 108 is executed. At 120, a third result 120 associated with the WSI 102 is generated.

In implementations, the first algorithm 104, the second algorithm 106, and the third algorithm 108 may be executed on various platforms located at various places. For example, the first algorithm 104 may be executed on a platform located in Germany. The second algorithm 106 may be executed on a platform located in Israel. The third algorithm 108 may be executed on a platform located executed in Brazil. Additionally or alternatively, the first algorithm 104, the second algorithm 106, and the third algorithm 108 may be executed on the same platform.

In implementations, the first result 112, the second result 116, and the third result 120 associated with the WSI 102 may be different types of results such as biomarker, cell segmentation, mitotic count, tissue boundary and patterns, and so on. For example, the first result 112 may include biomarker dots, which show biological molecules found in the WSI 102. The second result 116 may include cell segmentation, which split the image domain into segments that represent individual instances of cells in the WSI 102. The third result 120 may include tissue boundaries and patterns, which denote tissue regions of the WSI 102 identified for a particular purpose.

In stage III, the various results generated by executing the various algorithms may be integrated into the WSI 102. At 122, the first result 112, the second result 116, and the third result 120 may be integrated into the WSI 102 to generate a combined image. In implementations, the combined image may include at least one of the first result 112, the second result 116, and the third result 120. In implementations, the data of the WSI 102 and the first result 112, the second result 116, and the third result 120 may be saved together. The combined image may be displayed via a user interface of the digital pathology platform. The various results may be displayed in an overlapping manner. In some examples, the combined image may illustrate or overlay the results from different algorithms identifying different tissue boundaries and patterns, thereby enabling a user to quickly compare/contrast results.

Figure 1B:
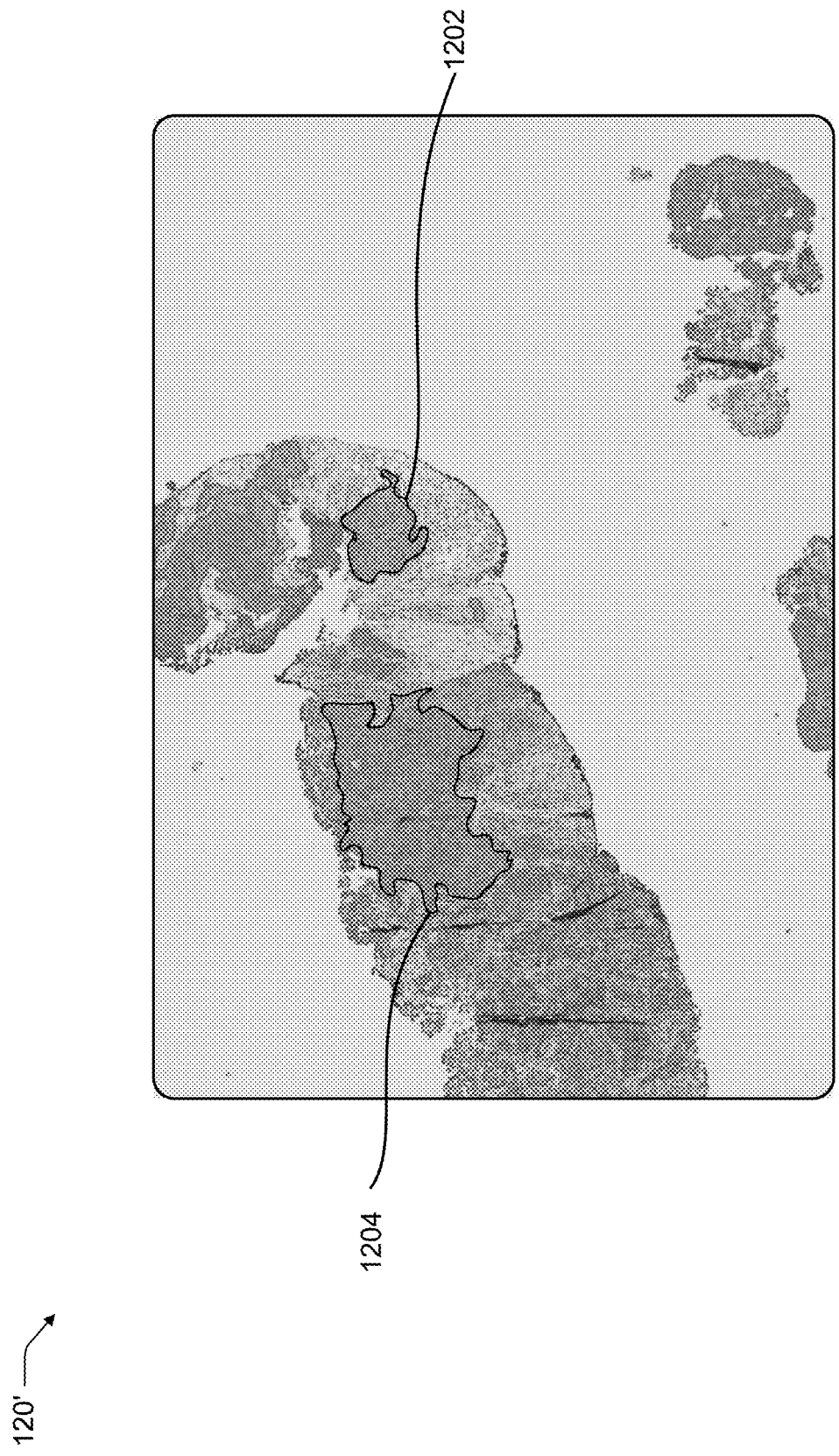
FIG. 1B illustrates an example result denoting tissue boundaries and patterns according to implementations of this disclosure.

FIG. 1B illustrates an example result 124 denoting tissue boundaries and patterns according to implementations of this disclosure. In implementations, the result 124 may be obtained by executing an algorithm that can identify tissue boundaries and patterns.

Referring to FIG. 1B the result 124 may include a first tissue boundary/pattern 126 and a second tissue boundary/pattern 128. In implementations, the first tissue boundary/pattern 126 and the second tissue boundary/pattern 128 may be the same type of first tissue boundary/pattern or different type of tissue boundaries/patterns. Though FIG. 1B shows two tissue boundaries/patterns, it should be understood that there may be other tissue boundaries/patterns. This disclosure is not limited thereto.

With the process 100, simultaneous execution of multi-vendors multi-algorithms image analysis on WSIs can be achieved. Various results can be integrated into a combined image to be displayed via the user interface on the digital pathology platform. The user may view the combined image with multi-vendors multi-algorithms results conveniently. The usability of the digital pathology platform can be improved. Moreover, combining the results into a single image (with selectable results) may save memory by storing a single WSI and then storing multiple results, rather than storing multiple WSIs and results for each algorithm.

Figure 2:
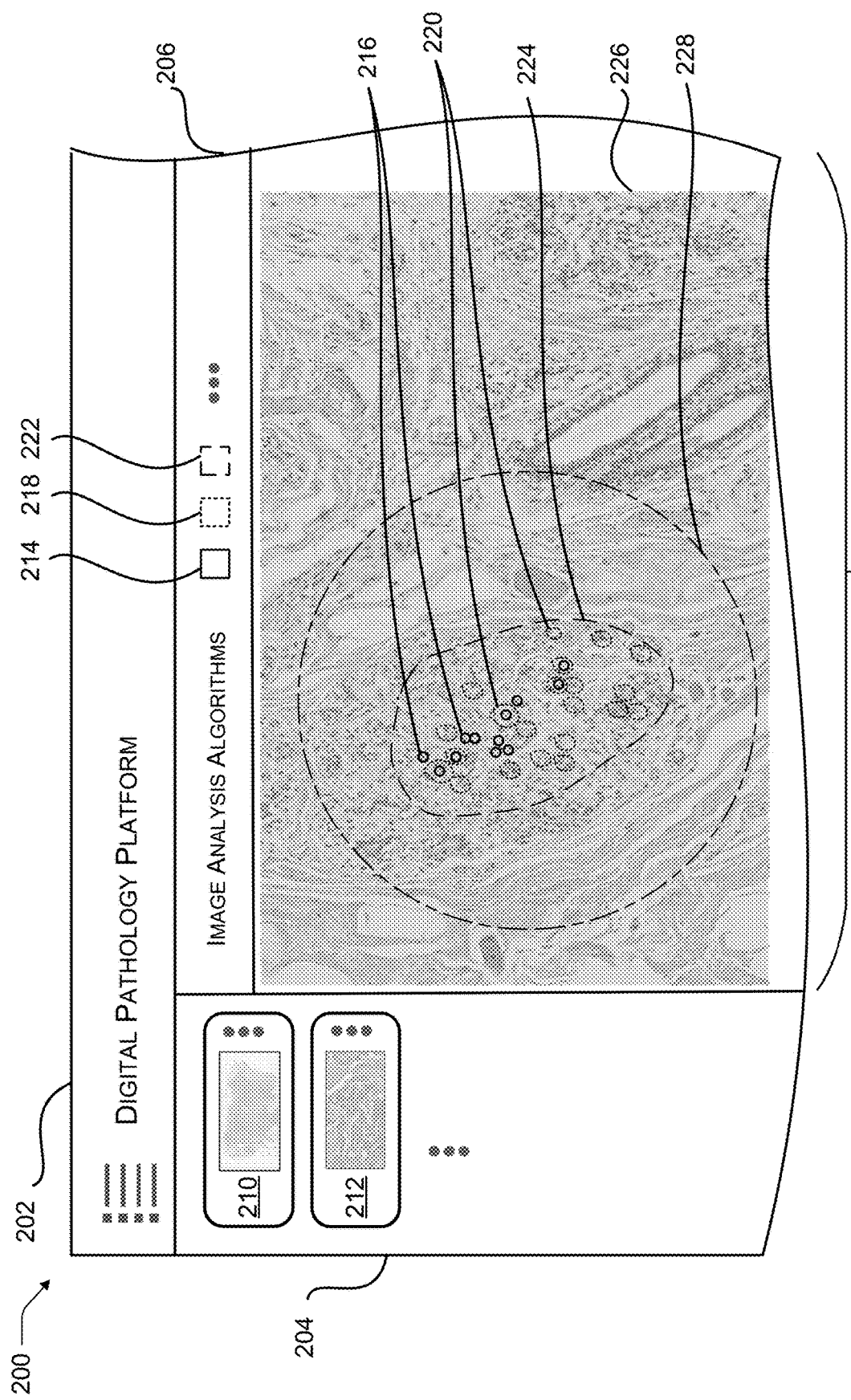
FIG. 2 illustrates an example user interface of a digital pathology platform showing a combined image according to implementations of this disclosure.

FIG. 2 illustrates an example user interface 200 of a digital pathology platform showing a combined image according to implementations of this disclosure.

Referring to FIG. 2, the user interface 200 of the digital pathology platform (e.g., PathFlow) may include a header 202, a sidebar 204, a toolbar 206, and the main display area 208. In implementations, the user interface 200 of the digital pathology platform may include other elements, such as pop-ups, scrolling bars, drop-down lists, status bars, start buttons, and so on.

The header 202 may be configured to show the name of the digital pathology platform (e.g., PathFlow). The sidebar 204 may be configured to show thumbnails of slide images such as a first slide image 210, a second slide image 212, and so on. The user may easily switch between slide images by clicking the thumbnails in the sidebar 204.

The toolbar 206 may be configured to show icons used to perform certain functions and allows for quick access to the functions. As described herein, the toolbar 206 may present different line types representing different results of various IA algorithms. For example, a first line type (e.g., solid line) 214 may represent a first result 216 of a first algorithm. Though reference number 216 points to solid lined circles in FIG. 2, this is for illustration purposes, and it should be understood that all the solid line circles belong to the first result 216. A second line type 218 (e.g., dotted line) may represent a second result 220 of a second algorithm. Though reference number 220 points to two dotted lined irregular shapes in FIG. 2, this is for illustration purposes, and it should be understood that all dotted line irregular shapes belong to the second result 220. A third line type 222 (e.g., dashed line) may represent a third result 224 of a third algorithm. Though reference number 224 points to two dashed lined irregular shapes in FIG. 2, this is for illustration purposes, and it should be understood that all dashed line irregular shapes belong to the third result 224. Though three line types (e.g., solid line, dotted line, and dashed line) are described here for representing different results, there may be other line types to represent various results. This disclosure is not limited thereto.

In implementations, the first result 216, the second result 220, and the third result 224 may be different types of results. For example, the first result 216 may be biomarker dots. The second result 220 may be cell segmentations. The third result 224 may be tissue boundaries and patterns. Additionally or alternatively, some or all of the second result 220, and the third results 224 may be the same type of results. For example, the first result 216 may be biomarker dots. The second result 220 may be cell segmentations. The third result 224 may also be cell segmentations but generated by a different third algorithm than the second algorithm that generates the second result 220. In implementations, the first algorithm, the second algorithm, and the third algorithm may be provided by different vendors or the same vendor. This disclosure is not limited thereto.

The main display area 208 may be configured to display the text, graphics, pictures, lights, and other background details to be viewed. In implementations, the main display area 208 may be configured to display slide images based on the user's operations. For example, when the user clicks the thumbnail of the first slide image 210, the main display area 208 may display the first slide image 210 in detail. When a user clicks the thumbnail of the second slide image 212, the main display area 208 may display the first slide image 212 in detail. As described herein, the main display area 208 may show a combined image 226 including the first result 216, the second result 220, and the third result 224 altogether. Additionally or alternatively, the main display area 208 may show the combined image 226 in a way that at least one of the first result 216, the second result 220, and the third result 224 is shown. The various results may be displayed in an overlapping manner. The main display area 208 may further show a region of interest (ROI) 228. The line type denoting the ROI 228 may be different than the line types that denote the results to avoid confusion. Though three results, i.e., the first result 216, the second result 220, and the third result 224 are shown in FIG. 2, this is for illustration purposes, and it should be understood that other numbers of results may be shown. In implementations, the combined image 226 may be obtained via the process 100 as described with respect to FIG. 1A.

Additionally, the combined image 226 is extensible. Results generated by new algorithms may be added to the combined image 226 via the user interface 200 of the digital pathology platform at any time, and results generated by existing algorithms may be removed from the combined image 226 via the user interface 200 of the digital pathology platform any time.

With the user interface 200, various results can be integrated into a combined image to be displayed via the user interface on the digital pathology platform. The user may view the combined image with multi-vendors multi-algorithms results conveniently. Thus, the usability of the digital pathology platform can be improved.

Figure 3:
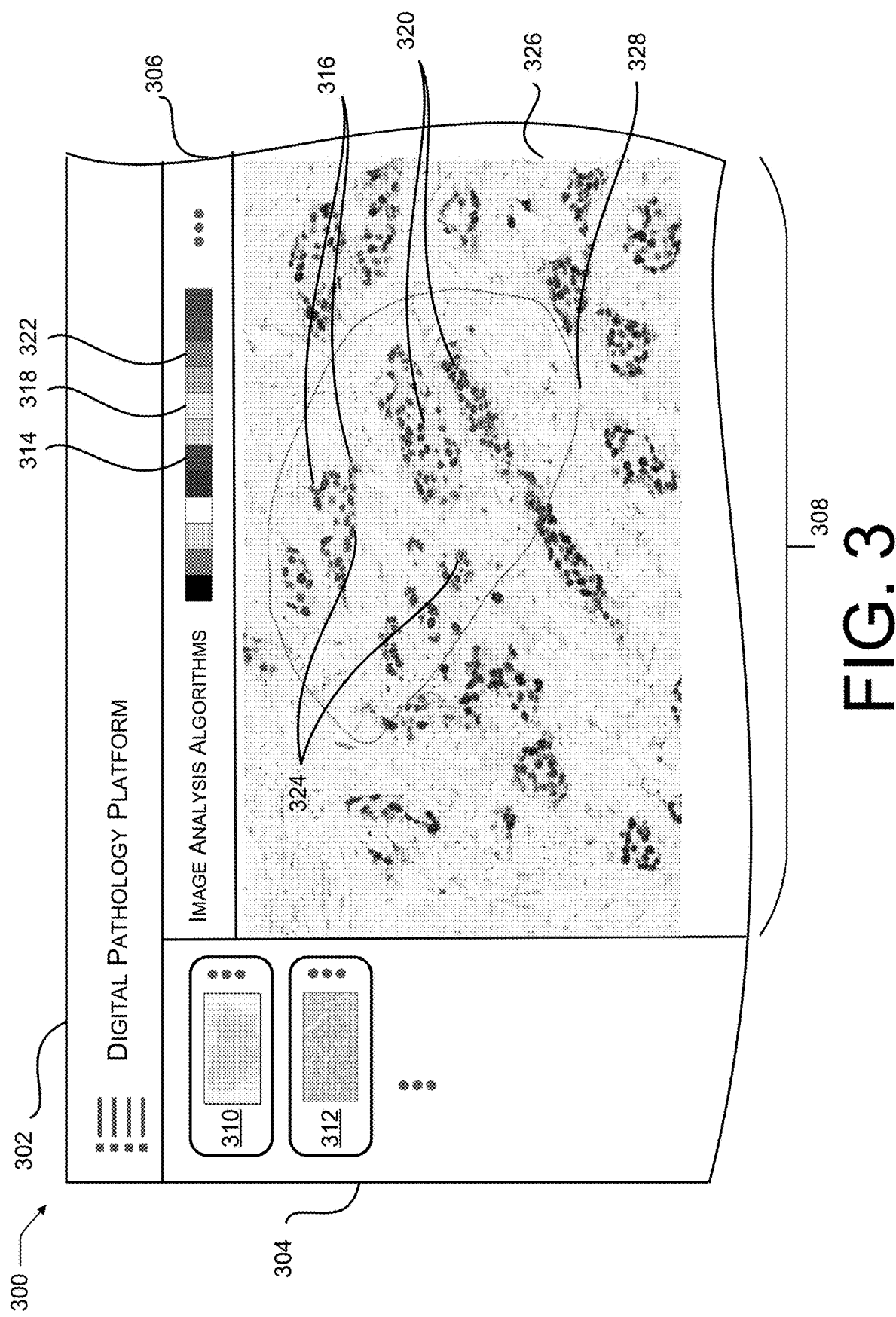
FIG. 3 illustrates an example user interface of a digital pathology platform showing a combined image according to implementations of this disclosure.

FIG. 3 illustrates an example user interface 300 of a digital pathology platform showing a combined image according to implementations of this disclosure.

Referring to FIG. 3, the user interface 300 of the digital pathology platform (e.g., PathFlow) may include a header 302, a sidebar 304, a toolbar 306, and a main display area 308. In implementations, the user interface 300 of the digital pathology platform may include other elements, such as pop-ups, scrolling bars, drop-down lists, status bars, start buttons, and so on.

The header 302 may be configured to show the name of the digital pathology platform (e.g., PathFlow). The sidebar 304 may be configured to show thumbnails of slide images such as a first slide image 310, a second slide image 312, and so on. The user may easily switch between slide images by clicking the thumbnails in the sidebar 304.

The toolbar 306 may be configured to show icons used to perform certain functions and allows for quick access to the functions. As described herein, the toolbar 306 may present a spectrum of colors representing results of various image analysis algorithms. For example, a first color (e.g., red) 314 may represent a first result 316 (e.g., the red solid dots) of a first algorithm. Though reference number 316 points to two red solid dots in FIG. 3, this is for illustration purposes, and it should be understood that all the red solid dots belong to the first result 316. A second color 318 (e.g., yellow) may represent a second result 320 (e.g., the yellow irregular shapes) of a second algorithm. Though reference number 320 points to two yellow irregular shapes in FIG. 3, this is for illustration purposes, and it should be understood that all yellow irregular shapes belong to the second result 320. A third color 322 (e.g., blue) may represent a third result 324 (e.g., the blue irregular shapes) of a third algorithm. Though reference number 324 points to two blue irregular shapes in FIG. 3, this is for illustration purposes, and it should be understood that all blue irregular shapes belong to the third result 324. Though three colors (e.g., red, yellow, and blue) are described here for representing different results, there may be other colors such as black, grey, white, orange, pink, green, navy, purple, and so on to represent various results. This disclosure is not limited thereto.

The main display area 308 may be configured to display the text, graphics, pictures, lights, and other background details to be viewed. The main display area 308 may be configured to display slide images based on the user's operations. For example, when the user clicks the thumbnail of the first slide image 310, the main display area 308 may display the first slide image 310 in detail. When a user clicks the thumbnail of the second slide image 312, the main display area 308 may display the first slide image 310 in detail. As described herein, the main display area 308 may show a combined image 326 including the first result 316, the second result 320, and the third result 324 altogether. Additionally or alternatively, the main display area 308 may show the combined image 326 in a way that at least one of the first result 316, the second result 320, and the third result 324 is shown. The various results may be displayed in an overlapping manner. The main display area 308 may further show an ROI 328. Though three results, i.e., the first result 316, the second result 320, and the third result 324 are shown in FIG. 3, it should be understood that other numbers of results may be shown. In implementations, the combined image 326 may be obtained via the process 100 as described with respect to FIG. 1A.

In implementations, each of the first results 316, the second result 320, and the third result 324 may be selected from different types of results such as biomarkers, mitotic cell count, cell segmentations, tissue boundaries and patterns, etc. For example, the first result 316 may be biomarker dots; the second result 320 may be cell segmentation; and the third result 324 may be tissue boundaries and patterns. Additionally or alternatively, some or all of the second result 320, and the third results 324 may be the same type of results. For example, the first result 316 may be biomarker dots; the second result 320 may be cell segmentation; and the third result 324 may also be cell segmentations but generated by a different third algorithm than the second algorithm that generates the second result 320. In implementations, the first algorithm, the second algorithm, and the third algorithm may be provided by different vendors or the same vendor. This disclosure is not limited thereto.

Additionally, the combined image 326 is extensible. Results generated by new algorithms may be added to the combined image 326 via the user interface 300 of the digital pathology platform at any time, and results generated by existing algorithms may be removed from the combined image 326 via the user interface 300 of the digital pathology platform any time.

With the user interface 300, various results can be integrated into a combined image to be displayed via the user interface on the digital pathology platform. The user may view the combined image with multi-vendors multi-algorithms results conveniently. Thus, the usability of the digital pathology platform can be improved.

Figure 4A:
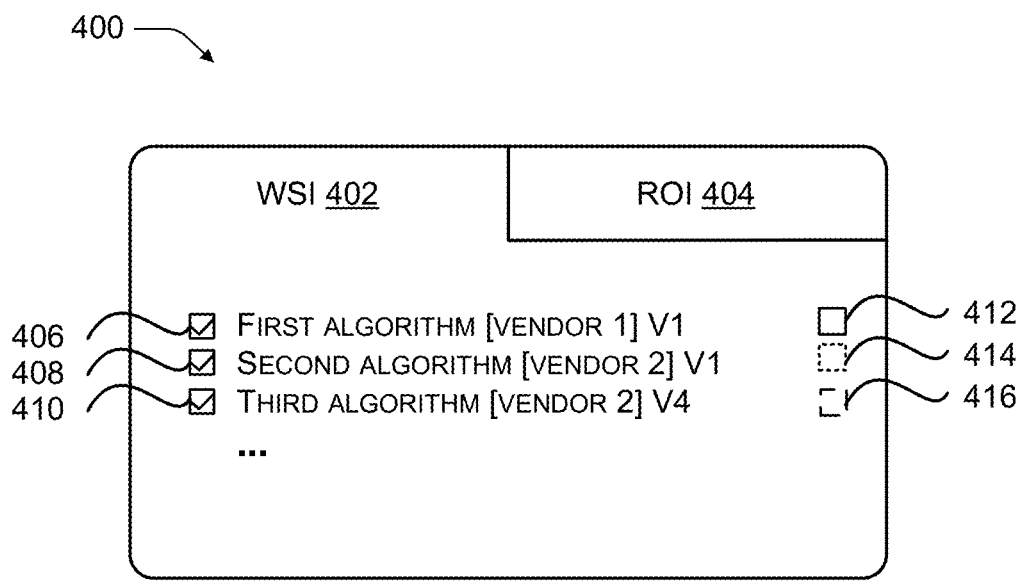
FIG. 4A and FIG. 4B illustrate an example popup that can be displayed in a user interface of a digital pathology platform.
Figure 4B:
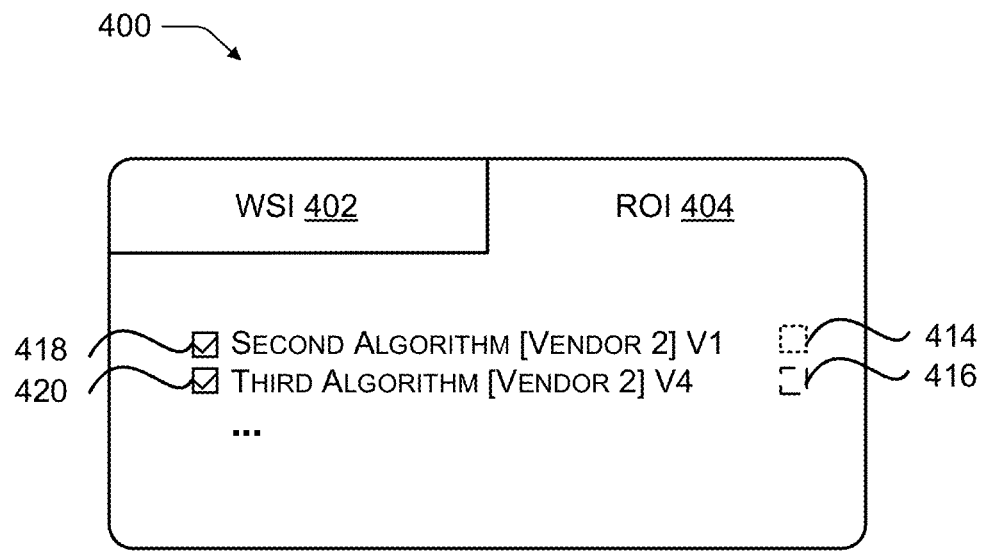

FIG. 4A and FIG. 4B illustrate an example popup 400 that can be displayed in a user interface of a digital pathology platform. As described herein, the popup is a graphical user interface display area that can appear as a window in different sizes and positions on the user interface. Referring to FIG. 4A and FIG. 4B, the popup 400 may include a WSI tab 402 and an ROI tab 404. Though FIG. 4A and FIG. 4B show two tabs, this is for illustration purpose, and it should be understood that the popup 400 may include other tabs. The user may conveniently switch between the WSI tab 402 and the ROI tab 404. The popup 400 may be configured to present multi-version, multi-algorithm, and multi-vendor results.

Referring to FIG. 4A, when the WSI tab 402 is selected, the popup 400 may present results generated by executing different algorithms regarding the WSI. For example, the popup 400 may present a first result of a first algorithm (e.g., mitotic cell count) provided by a first vendor (e.g., Vendor 1) in version 1, a second result of a second algorithm (e.g., breast biomarker) provided by a second vendor (e.g., Vendor 2) in version 1, and a third result of a third algorithm (e.g., Breast biomarker) provided by the second vendor (e.g., Vendor 2) in version 4. In implementations, the first algorithm, the second algorithm, and the third algorithm may be provided by the same vendor or different vendors. Though FIG. 4A shows three results, this is for illustration purposes, and it should be understood that other numbers of results may be shown.

In implementations, the user may operate on the results to show or hide the results in the WSI via the user interface of the digital pathology platform. For example, when the first checkbox 406 is checked, the first result of the first algorithm (e.g., mitotic cell count) may be shown in the WSI via the user interface of the digital pathology platform. When the first checkbox 406 is unchecked, the first result of the first algorithm (e.g., mitotic cell count) may be hidden in the WSI via the user interface of the digital pathology platform. For example, when the second checkbox 408 is checked, the second result of the second algorithm (e.g., breast biomarker) may be shown in the WSI via the user interface of the digital pathology platform. When the second checkbox 408 is unchecked, the second result of the second algorithm (e.g., breast biomarker) may be hidden in the WSI via the user interface of the digital pathology platform. For example, when the third checkbox 410 is checked, the third result of the third algorithm (e.g., breast biomarker) may be shown in the WSI via the user interface of the digital pathology platform. When the third checkbox 410 is unchecked, the third result of the third algorithm (e.g., breast biomarker) may be hidden in the WSI via the user interface of the digital pathology platform.

In implementations, the first result, the second result, and the third result may be represented by different line types. For example, the first result of the first algorithm (e.g., mitotic cell count) may be represented by a first line type (e.g., solid line) 412. The second result of the second algorithm (e.g., breast biomarker) may be represented by a second line type 414 (e.g., dotted line). The third result of the third algorithm (e.g., breast biomarker) may be represented by a third line type 416 (e.g., dashed line). Additionally or alternatively, the first result, the second result, and the third result may be represented by different colors.

Referring to FIG. 4B, when the ROI tab 404 is selected, the popup 400 may present results generated by executing different algorithms regarding the ROI. For example, the popup 400 may present the second result of the second algorithm (e.g., breast biomarker) provided by the second vendor (e.g., Vendor 2) in version 1, and the third result of the third algorithm (e.g., Breast biomarker) provided by the second vendor (e.g., Vendor 2) in version 4. In implementations, the second algorithm and the third algorithm may be provided by the same vendor or different vendors. Though FIG. 4B shows two results, this is for illustration purposes, and it should be understood that other numbers of results may be shown.

In implementations, the user may operate on the results to show or hide the results in the ROI via the user interface of the digital pathology platform. For example, when the fourth checkbox 418 is checked, the second result of the second algorithm (e.g., breast biomarker) may be shown in the ROI via the user interface of the digital pathology platform. When the fourth checkbox 418 is unchecked, the second result of the second algorithm (e.g., breast biomarker) may be hidden in the ROI via the user interface of the digital pathology platform. For example, when the fifth checkbox 420 is checked, the third result of the third algorithm (e.g., breast biomarker) may be shown in the ROI via the user interface of the digital pathology platform. When the fifth checkbox 420 is unchecked, the third result of the third algorithm (e.g., breast biomarker) may be hidden in the ROI via the user interface of the digital pathology platform. Although checkboxes are used to control the shown/hidden states of results, it should be understood that other mechanisms can be used to control the shown/hidden states of results, for example, buttons, sliders, icons, and so on.

In implementations, the second result and the third result may be represented by different line types. For example, the second result of the second algorithm (e.g., breast biomarker) may be represented by a second line type 414 (e.g., dotted line). The third result of the third algorithm (e.g., breast biomarker) may be represented by a third line type 222 (e.g., dashed line). Additionally or alternatively, the second result and the third result may be represented by different colors.

With the popup 400, the user may conveniently operate on the results to control which result is shown/hidden in the WSI and ROI via the user interface of the digital pathology platform. The usability of the digital pathology platform can be improved.

Figure 5:
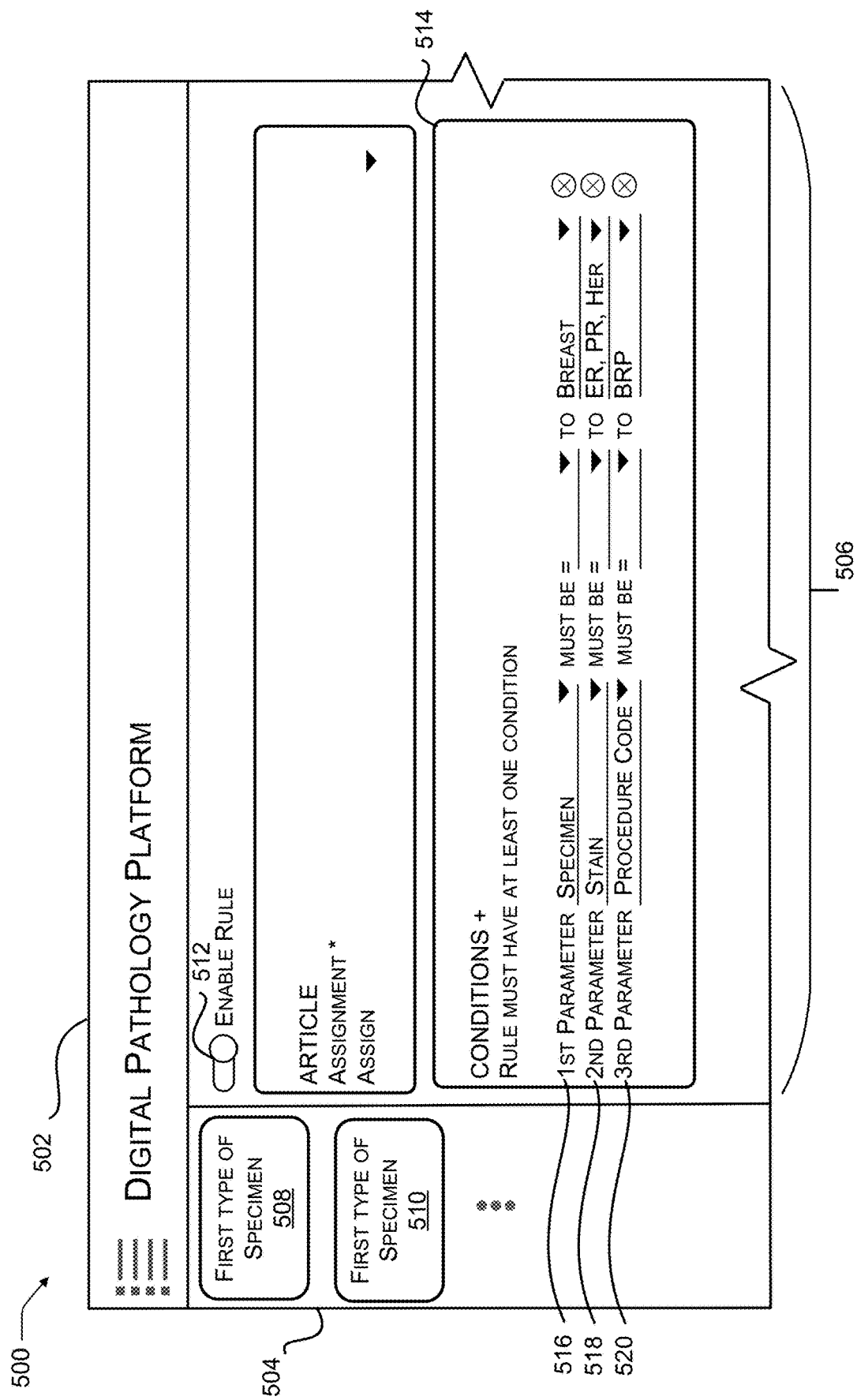
FIG. 5 illustrates an example user interface of a digital pathology platform showing a rule setting environment according to implementations of this disclosure.

FIG. 5 illustrates an example user interface 500 of a digital pathology platform showing a rule setting environment according to implementations of this disclosure.

Referring to FIG. 5, the user interface 500 of the digital pathology platform (e.g., PathFlow) may include a header 502, a sidebar 504, and a main display area 506. In implementations, the user interface 500 of the digital pathology platform may include other elements, such as pop-ups, scrolling bars, drop-down lists, status bars, start buttons, and so on.

The header 502 may be configured to show the name of the digital pathology platform (e.g., PathFlow). The sidebar 504 may be configured to show different types of specimens for which rules are to be set. As an example, the sidebar 504 may present a first type of specimen (e.g., breast tissue) 508, a second type of specimen (e.g., prostate tissue) 510, and so on. The user may conveniently select different types of specimens in the sidebar 504 to set rules for each type of specimen.

The main display area 506 may be configured to display the text, graphics, pictures, lights, and other background details to be viewed. As described herein, the main display area 308 may be configured to display the rule setting environment. In implementations, the rules may include various parameters indicating specimen types, stain types, procedure codes, vendors, algorithms, and so on. In the main display area 506, a slider 512 may be configured to indicate whether the rules are enabled or disabled. Additionally, the slider 512 may be operable to switch enable or disable the rules.

For example, the user may select the first type of specimen (e.g., breast tissue) 508 to set rules for the first type of specimen (e.g., breast tissue) 508. When the first type of specimen 508 is selected, rules associated with the first type of specimen 508 may be set in section 514 using parameters. As an example, in section 514, a first parameter 516 may indicate that the specimen type is breast. A second parameter 518 may indicate that the stain type is ER, PR, Her. A third parameter 520 may indicate that the procedure code. Procedure codes are associated with a Pathology Case to classify it in terms of tissue type, specialization of Pathologist, and other criteria as determined by the customer. A "Procedure Code" schema will vary between implementations. In implementations, the user can use dropdown lists to select different parameters to define the rules. Additionally or alternatively, the user may delete/add parameters. Though three parameters are shown in FIG. 5, it should be understood that other parameters may be included, such as the organization, the referring physician, and so on. This disclosure is not limited thereto.

Additionally, rules associated with the second type of specimen (e.g., prostate tissue) 510 may be set similarly.

With the user interface 500, the rules may be set regarding how to assign various algorithms to various WSIs based on parameters such as the specimen type, the stain type, the procedure code, and so on. In practice, the user may view, edit, add, and/or delete the rules via the user interface 500 of the digital pathology platform. Moreover, after the rules are set, the digital pathology platform may assign various algorithms to various WSIs based on the rules automatically without intervening from the user. Therefore, when there are a great number of WSIs to be processed, the digital pathology platform may assign the algorithms to the WSIs efficiently. Thus, the usability of the digital pathology platform is improved.

FIG. 6 is an example table 600 showing the corresponding relationship of vendors, algorithms, versions, slide IDs, and status according to implementations of this disclosure.

Referring to FIG. 6, column 602 shows vendors. Column 604 shows algorithms. Column 606 shows versions of algorithms. Column 608 shows slide IDs of the WSI. Column 610 shows the status of WSIs. In implementation, "status" may indicate whether the execution of an algorithm on a WSI is complete and results are ready for the digital pathology platform. For example, when a checkbox is checked in the status column, that means that the execution of the algorithm on the WSI is complete and results are ready for the digital pathology platform. Additionally or alternatively, when a checkbox is unchecked in the status column, that means that the execution of the algorithm on the WSI is complete and results are ready for the digital pathology platform.

Row 612 shows that the vendor is Vendor 2; the algorithm is the first algorithm (e.g., Breast BioM); the version of the algorithm is 1.0; the slide ID is the second WSI ID (e.g., A1-IMH-2); and the status is checked. Row 614 shows that the vendor is Vendor 1; the algorithm is the first algorithm (e.g., Breast BioM); the version of the algorithm is 1.0; the slide ID is the first WSI ID (e.g., A1-IMH-1); and the status is checked. Row 616 shows that the vendor is Vendor 2; the algorithm is the second algorithm (e.g., Mitotic #); the version of the algorithm is 2.0; the slide ID is the first WSI ID (e.g., A1-IMH-1); and the status is checked. Row 618 shows that the vendor is Vendor 1; the algorithm is the first algorithm (e.g., Breast BioM); the version of the algorithm is 1.0; the slide ID is the second WSI ID (e.g., A1-IMH-2); and the status is checked. Row 620 shows that the vendor is Vendor 1; the algorithm is the first algorithm (e.g., Breast BioM); the version of the algorithm is 1.0; the slide ID is the second WSI ID (e.g., A1-IMH-2); and the status is checked. Row 622 shows that the vendor is Vendor 2; the algorithm is the second algorithm (e.g., Mitotic #); the version of the algorithm is 2.0; the slide ID is the second WSI ID (e.g., A1-IMH-2); and the status is checked. Row 624 shows that the vendor is Vendor 3; the algorithm is the second algorithm (e.g., Mitotic #); the version of the algorithm is 1.0; the slide ID is the third WSI ID (e.g., A1-IMH-3); and the status is checked. Row 626 shows that the vendor is Vendor 2; the algorithm is the second algorithm (e.g., Mitotic #); the version of the algorithm is 2.0; the slide ID is the fourth WSI ID (e.g., A1-IMH-4); and the status is checked.

Though table 600 shows three vendors, two algorithms, two versions of algorithms, four slide IDs, this is for illustration purposes, and it should be understood that there may be other numbers of vendors, algorithms, versions of algorithms, slide IDs. Additionally, other information may be included in the table, such as the specimen type of the WSI, the stain type of the specimen, and so on. This disclosure is not limited thereto.

In the table 600, multiple algorithms from multiple vendors may be assigned to the same WSI. For example, the first algorithm (e.g., Breast BioM) from Vendor 1 and the second algorithm (e.g., Mitotic #) from Vendor 2 are assigned to the first WSI (e.g., A1-IMH-1).

In implementations, the table 600 may be maintained by the digital pathology platform. With the table 600, the user may review the corresponding relationship of vendors, algorithms, versions, slide IDs, and status on the digital pathology platform conveniently. Moreover, the table 600 is extensible, new algorithms may be added and existing algorithms may be removed at any time. Thus, the usability of the digital pathology platform is improved.

Figure 7:
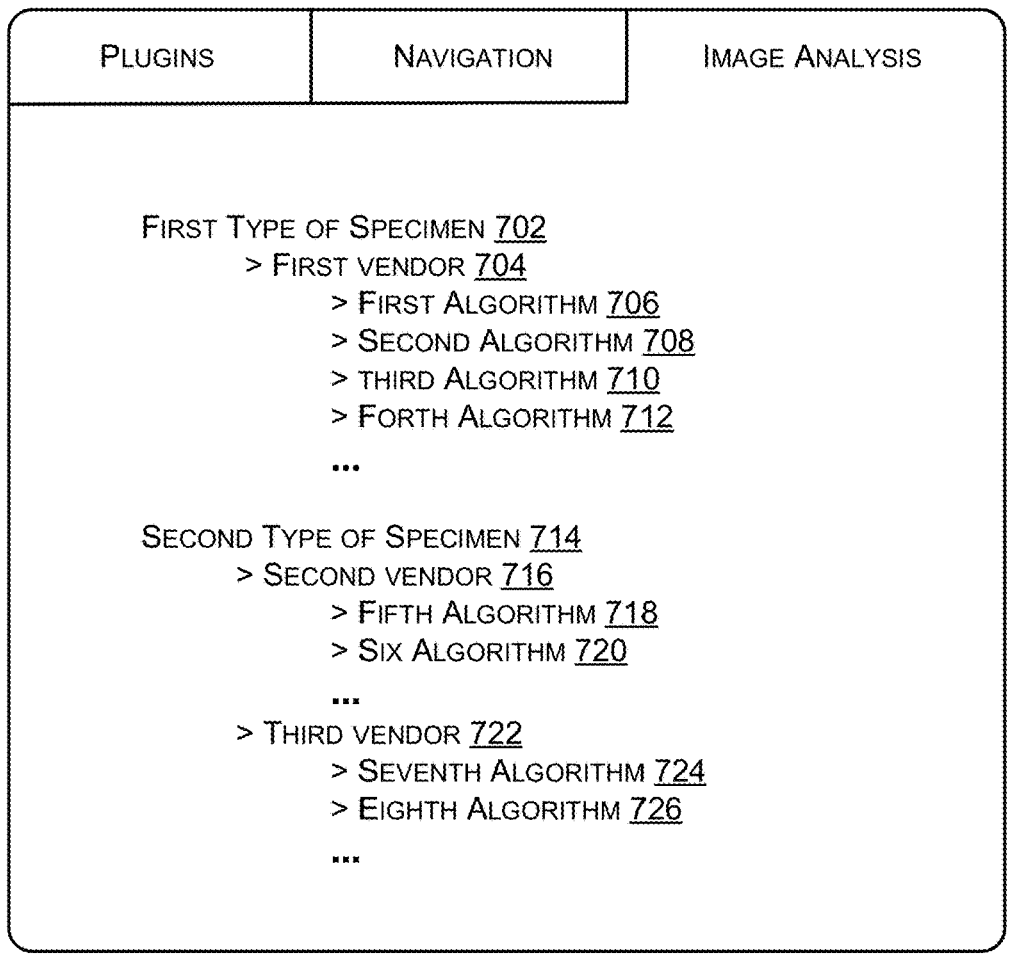
FIG. 7 is an example popup showing various algorithms from various vendors are assigned to various types of specimens according to implementations of this disclosure.

FIG. 7 is an example popup 700 showing various algorithms from various vendors are assigned to various types of specimens according to implementations of this disclosure.

Referring to FIG. 7, the first type of specimen 702 may be assigned algorithms from a first vendor 704, including a first algorithm 706, a second algorithm 708, a third algorithm 710, a fourth algorithm 712, and so on. A second type of specimen 714 may be assigned algorithms from a second vendor 716 and algorithms from a third vendor 722. Algorithms from the second vendor 716 assigned to the second type of specimen 714 may include a fifth algorithm 718, a sixth algorithm 170, and so on. Algorithms from the third vendor 722 assigned to the second type of specimen 714 may include a seventh algorithm 724, an eighth algorithm 726, and so on.

With the popup 700, the corresponding relationship between the specimen type, the vendor, and the algorithm may be presented via the user interface of the digital pathology platform. In practice, the user may view, edit, add, and/or delete which algorithm is assigned to which specimen type. Thus, the usability of the digital pathology platform is improved.

Figure 8A:
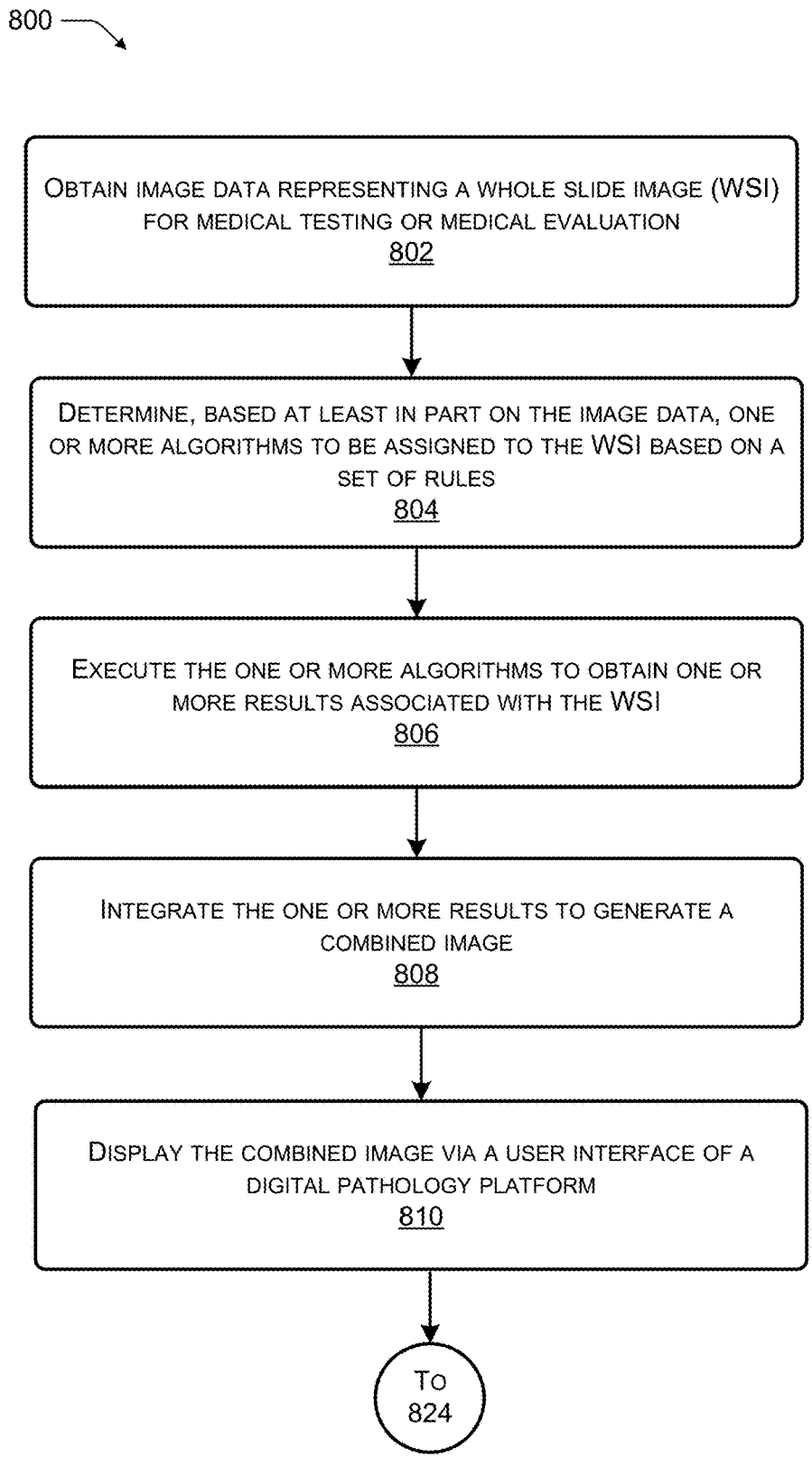

FIG. 8A, FIG. 8B, FIG. 8C, FIG. 8D, and FIG. 8E illustrate an example process 800 for enhancing the digital pathology platform according to implementations of this disclosure. Referring to FIG. 8A, process 800 may include the following.

At 802, operations may include obtaining image data representing a WSI for medical testing or medical evaluation. For example, the WSI may be a digital slide obtained by scanning of conventional glass slides, and include information/data regarding a specimen. The WSI may correspond to the slide images described throughout this disclosure such as in FIGS. 1-7.

At 804, operations may include determining, based at least in part on the image data, one or more algorithms to be assigned to the WSI based on a set of rules. In implementations, the set of rules includes at least one of specimen type associated with the WSI, a stain type associated with the WSI, and/or a procedure code associated with the WSI. In implementations, the rules may be set regarding how to assign various algorithms to various WSIs based on parameters such as the specimen type, the stain type, the procedure code, and so on. In practice, the user may view, edit, add, and/or delete the rules via the user interface of the digital pathology platform. Additional details are given throughout this disclosure such as with reference to FIG. 5.

In implementations, the corresponding relationship of vendors, algorithms, versions, slide IDs, and status may be saved in a table (such as the table 600 described with reference to FIG. 6). The table may be maintained by the digital pathology platform. The user may review the corresponding relationship of vendors, algorithms, versions, slide IDs, and status on the digital pathology platform conveniently. Additional details are given throughout this disclosure such as with reference to FIG. 6.

In implementations, the corresponding relationship between the specimen type, the vendor, and the algorithm may be presented via the user interface of the digital pathology platform. In practice, the user may view, edit, add, and/or delete which algorithm is assigned to which specimen type. Additional details are given throughout this disclosure such as with reference to FIG. 7.

At 806, operations may include executing the one or more algorithms to obtain one or more results associated with the WSI. In implementations, the one or more algorithms may be executed in parallel. Additionally or alternatively, the one or more algorithms may be executed sequentially. In implementations, new algorithms may be added to be executed at any time, and existing algorithms may be removed to be executed at any time. Moreover, the execution of algorithms is configurable by enabling or disabling the algorithms. In implementations, the one or more algorithms may be executed on different platforms. In implementations, the one or more algorithms may be provided by different vendors, and the different vendors may have different platforms to run the algorithms. In implementations, the one or more algorithms may be executed at different places. For example, a first algorithm may be executed on a platform located in Germany. a second algorithm may be executed on a platform located in Israel. A third algorithm may be executed on a platform located executed at Brazil. Additionally or alternatively, the one or more algorithms may be executed on the same platform.

At 808, operations may include integrating the one or more results to generate a combined image. In implementations, the one or more results include different types of results such as biomarker, cell segmentation, mitotic count, tissue boundaries and patterns, and so on. For example, the first result may include biomarker dots, which show biological molecules found in the WSI. The second result may include cell segmentation, which split the image domain into segments that represent individual instances of cells in the WSI. The third result may include tissue boundaries and patterns, which denote tissue regions of the WSI identified for a particular purpose. In implementations, the one or more results may be presented in an overlapping manner.

At 810, operations may include displaying the combined image via a user interface of a digital pathology platform. Additional details regarding the combined image are given throughout this disclosure.

Figure 8B:
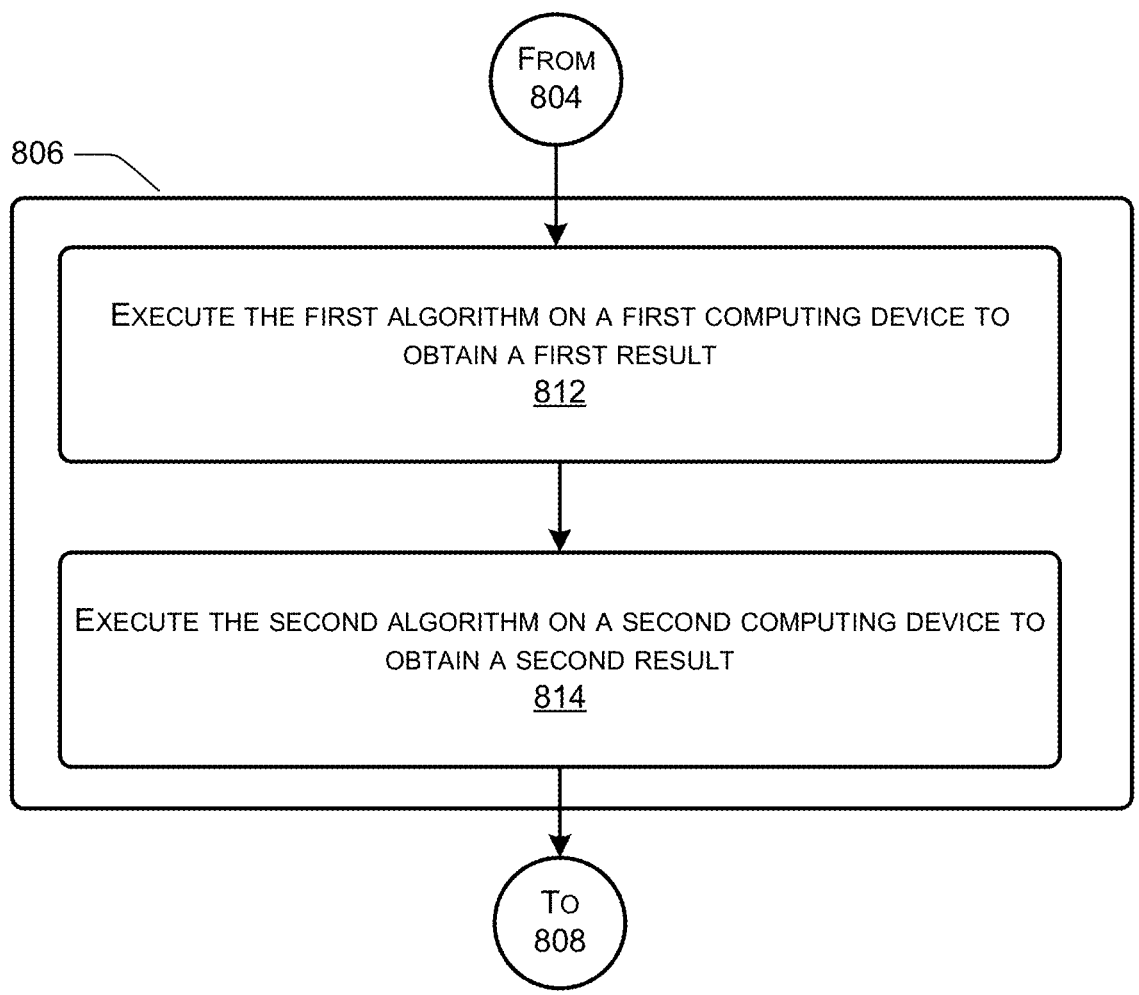

Referring to FIG. 8B, 806 may include the following. At 812, operations may include executing the first algorithm on a first computing device to obtain a first result. At 814, operations may include executing the second algorithm on a second computing device to obtain a second result. In implementations, the first and second algorithms may be executed in parallel. Additionally or alternatively, the first and second algorithms may be executed sequentially. In implementations, new algorithms may be added to be executed at any time, and existing algorithms may be removed at any time. Moreover, the execution of algorithms is configurable by enabling or disabling the algorithms.

Figure 8C:
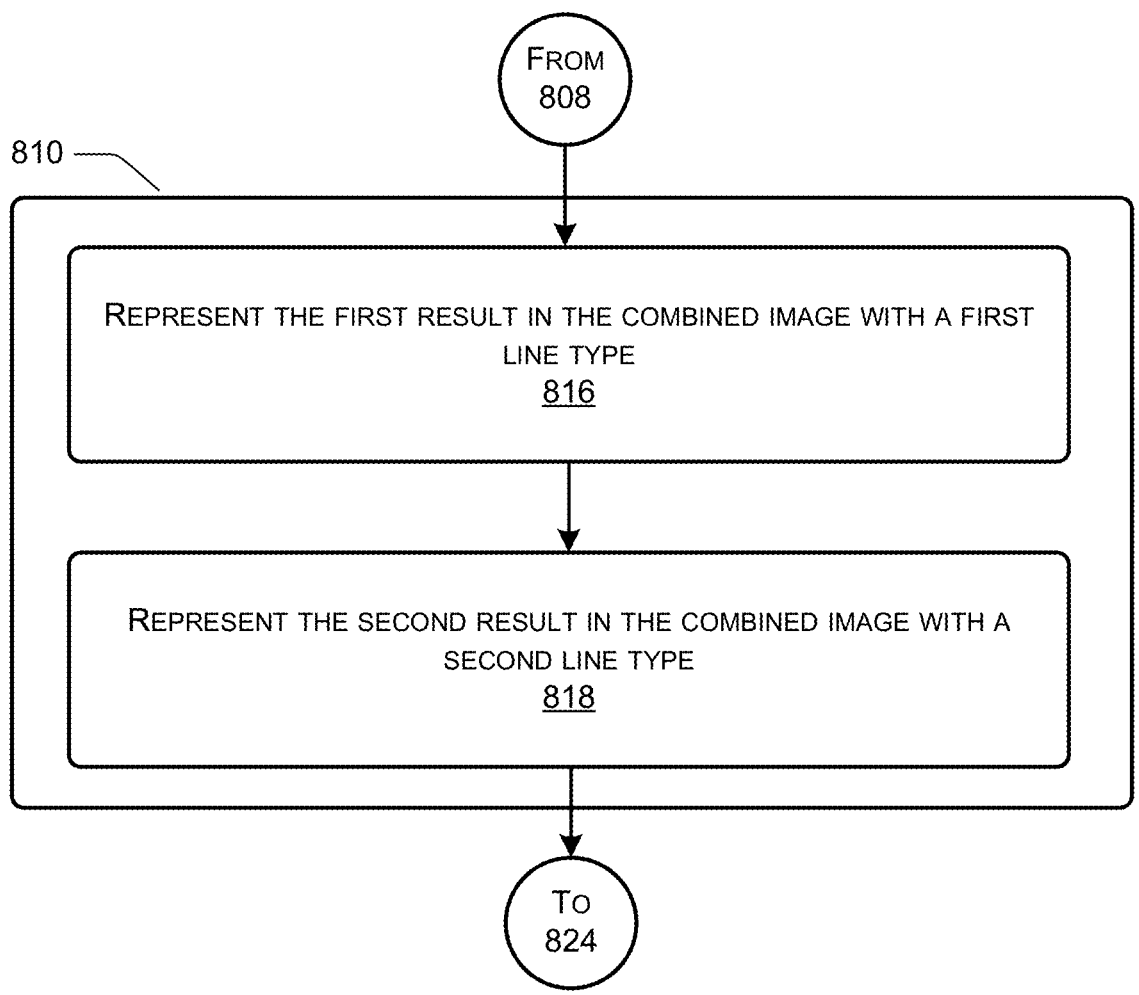

Referring to FIG. 8C, 810 may include the following. At 816, operations may include representing the first result in the combined image with a first line type. At 818, operations may include representing the second result in the combined image with a second line type.

In implementations, the one or more results may be displayed in the combined image via the user interface of the digital pathology platform in different line types. For example, a first line type (e.g., solid line) may represent a first result of a first algorithm. A second line type (e.g., dotted line) may represent a second result of a second algorithm. Additionally, there may be other line types to represent other results. This disclosure is not limited thereto. Additional details are given throughout this disclosure, such as with reference to FIG. 2.

Referring to FIG. 8C, 810 may include the following. At 820, operations may include representing the first result in the combined image with a first color. At 822, operations may include representing the second result in the combined image with a second color.

In implementations, the one or more results may be displayed in the combined image via the user interface of the digital pathology platform in different colors. For example, a first color (e.g., red) may represent a first result 316 of a first algorithm. A second color (e.g., yellow) may represent a second result of a second algorithm. Additionally, there may be other colors such as black, grey, white, orange, pink, green, navy, purple, and so on to represent other results. This disclosure is not limited thereto. More details are given throughout this disclosure, such as with reference to FIG. 3.

Referring to FIG. 8E, the process 800 may further include the following. At 824, operations may include presenting a graphical element to selectively display the first result via the user interface of the digital pathology platform. For example, the operation may be conducted by the user by clicking a checkbox. Additional details are given throughout this disclosure, such as with reference to FIG. 4A and FIG. 4B.

At 826, operations may include receiving an indication of a selection of the graphical element. For example, when a first checkbox is checked, a first result may be shown in the combined image via the user interface of the digital pathology platform. When the first checkbox is unchecked, the first result may be hidden in the combined image via the user interface of the digital pathology platform. More details are given throughout this disclosure, such as with reference to FIG. 4A and FIG. 4B.

Figure 8D:
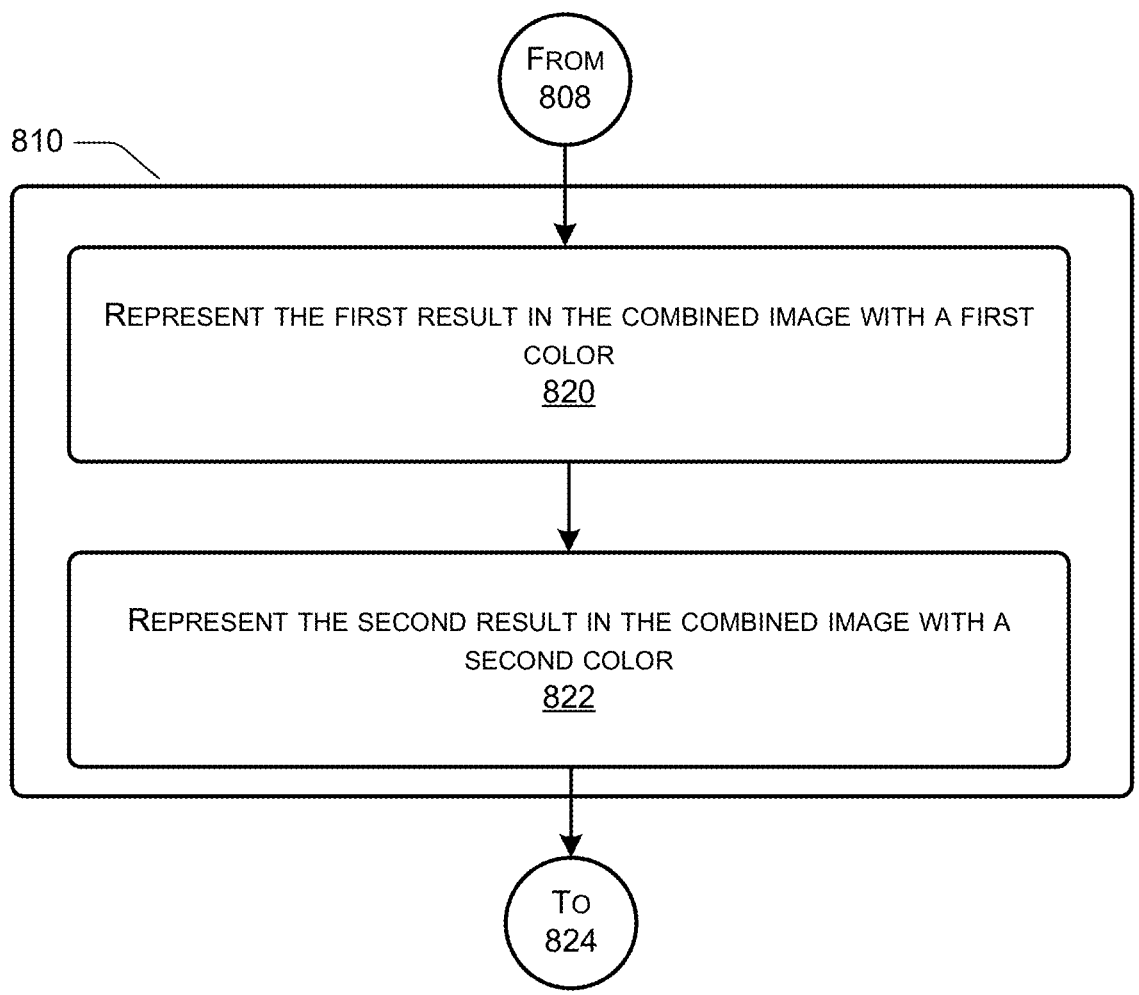

Referring to FIG. 8D, the process 800 may further include the following. At 824, operations may include presenting a graphical element to selectively display the first result via the user interface of the digital pathology platform. For example, the graphical element may include checkboxes, buttons, sliders, icons, and other mechanisms that are suitable for controlling the shown/hidden states of results.

At 826, operations may include receiving an operation of showing/hiding the second result. At 828, operations may include based at least in part on the indication, performing at least one of showing or hiding the first result in the combined image via the user interface of the digital pathology platform. In implementations, the user may operate the graphical element to indicate whether the results should be shown/hidden from the combined image. As an example, the graphical element may include checkboxes. When a first checkbox is checked, the first result may be shown in the combined image via the user interface of the digital pathology platform. When the first checkbox is unchecked, the first result may be hidden in the combined image via the user interface of the digital pathology platform. When a second checkbox is checked, the second result may be shown in the combined image via the user interface of the digital pathology platform. When the second checkbox is unchecked, the second result may be hidden in the combined image via the user interface of the digital pathology platform. Additional details are given throughout this disclosure, such as with reference to FIG. 4A and FIG. 4B.

With the process 800, algorithms may be assigned to the WSI automatically based on a set of rules, and simultaneous execution of multi-vendors multi-algorithms image analysis on WSIs can be achieved. Various results can be integrated into a combined image to be displayed via the user interface on the digital pathology platform. The user may view the combined image with multi-vendors multi-algorithms results conveniently and control the results to be shown/hidden in the combined image. Moreover, the user may view and edit the rules regarding which algorithm is assigned to which type of specimen via the user interface on the digital pathology platform. Thus, the usability of the digital pathology platform can be improved.

Figure 9:
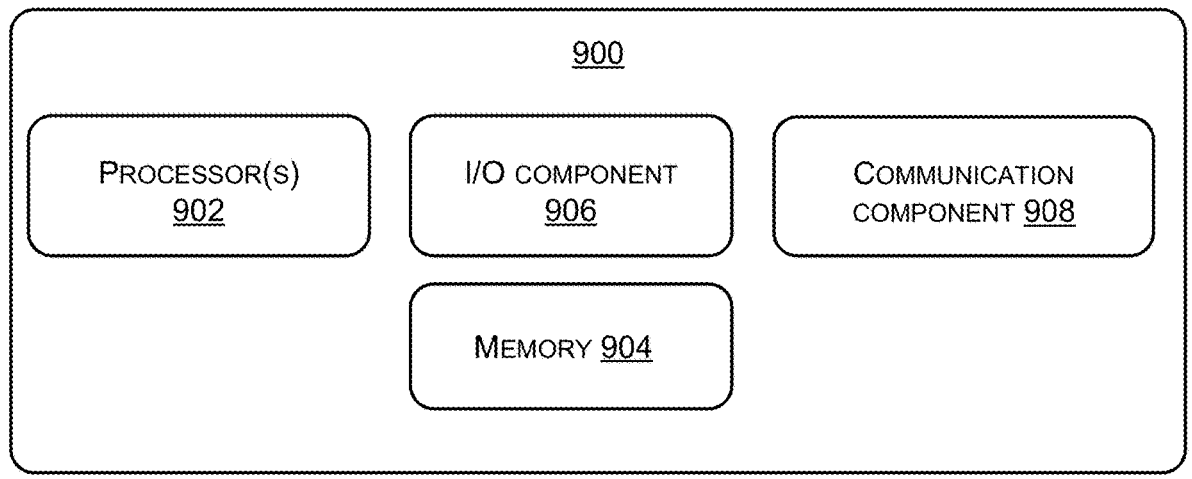
FIG. 9 illustrates an example apparatus for implementing the processes and methods described above.

FIG. 9 illustrates an example apparatus 900 for implementing the processes and methods described above.

The techniques and mechanisms described herein may be implemented by multiple instances of the apparatus 900 as well as by any other computing device, system, and/or environment. The apparatus 900 shown in FIG. 9 is only one example of a system and is not intended to suggest any limitation as to the scope of use or functionality of any computing device utilized to perform the processes and/or procedures described above. Other well-known computing devices, systems, environments, and/or configurations that may be suitable for use with the embodiments include, but are not limited to, personal computers, server computers, hand-held or laptop devices, multiprocessor systems, microprocessor-based systems, set top boxes, game consoles, programmable consumer electronics, network PCs, minicomputers, mainframe computers, distributed computing environments that include any of the above systems or devices, implementations using field programmable gate arrays ("FPGAs") and application specific integrated circuits ("ASICs"), and/or the like.

The apparatus 900 may include one or more processors 902 and system memory 904 communicatively coupled to the processor(s) 902. The processor(s) 902 may execute one or more components and/or processes to cause the processor(s) 902 to perform a variety of functions. In some embodiments, the processor(s) 902 may include a central processing unit (CPU), a graphics processing unit (GPU), both CPU and GPU, or other processing units or components known in the art. Additionally, each of the processor(s) 902 may possess its own local memory, which also may store program components, program data, and/or one or more operating systems.

Depending on the exact configuration and type of the apparatus 900, the system memory 904 may be volatile, such as RAM, non-volatile, such as ROM, flash memory, miniature hard drive, memory card, and the like, or some combination thereof. The system memory 904 may include computer-readable instructions that are executable by the processor(s) 902. When executed by one or more processors, the computer-readable instructions cause the one or more processors to perform processes and/or operations described herein.

The apparatus 900 may additionally include an input/output (I/O) interface 906 for receiving data to be processed, and for outputting the processed data. The apparatus 900 may also include a communication component 908 allowing the apparatus 900 to communicate with other devices (not shown) over a network (not shown). The network may include the Internet, wired media such as a wired network or direct-wired connections, and wireless media such as acoustic, radio frequency (RF), infrared, and other wireless media.

Some or all operations of the methods described above may be performed by execution of computer-readable instructions stored on a computer-readable storage medium, as defined below. The term "computer-readable instructions" as used in the description and claims, includes routines, applications, application modules, program modules, programs, components, data structures, algorithms, and the like. Computer-readable instructions may be implemented on various system configurations, including single-processor or multiprocessor systems, minicomputers, mainframe computers, personal computers, hand-held computing devices, microprocessor-based, programmable consumer electronics, combinations thereof, and the like.

The computer-readable storage media may include volatile memory (such as random access memory (RAM)) and/or non-volatile memory (such as read-only memory (ROM), flash memory, etc.). The computer-readable storage media may also include additional removable storage and/or non-removable storage including, but is not limited to, flash memory, magnetic storage, optical storage, and/or tape storage that may provide non-volatile storage of computer-readable instructions, data structures, program modules, and the like.

A non-transitory computer-readable storage medium is an example of computer-readable media. Computer-readable media includes at least two types of computer-readable media, namely computer-readable storage media and communications media. Computer-readable storage media includes volatile and non-volatile, removable and non-removable media implemented in any process or technology for storage of information such as computer-readable instructions, data structures, program modules, or other data. Computer-readable storage media includes, but is not limited to, phase-change memory (PRAM), static random-access memory (SRAM), dynamic random-access memory (DRAM), other types of random-access memory (RAM), read-only memory (ROM), electrically erasable programmable read-only memory (EEPROM), flash memory or other memory technology, compact disc read-only memory (CD-ROM), digital versatile discs (DVD) or other optical storage, magnetic cassettes, magnetic tape, magnetic disk storage or other magnetic storage devices, or any other non-transmission medium that may be used to store information for access by a computing device. In contrast, communication media may embody computer-readable instructions, data structures, program modules, or other data in a modulated data signal, such as a carrier wave, or other transmission mechanisms. As defined herein, computer-readable storage media do not include communication media.

The computer-readable instructions are stored on one or more non-transitory computer-readable storage media that, when executed by one or more processors, may perform operations described above with reference to the drawings. Generally, computer-readable instructions include routines, programs, objects, components, data structures, and the like that perform particular functions or implement particular abstract data types. The order in which the operations are described is not intended to be construed as a limitation, and any number of the described operations may be omitted or combined in any order and/or in parallel to implement the processes.

CONCLUSION

Although the subject matter has been described in language specific to structural features and/or methodological acts, it is to be understood that the subject matter defined in the appended claims is not necessarily limited to the specific features or acts described. Rather, the specific features and acts are disclosed as illustrative forms of implementing the claims.

Example Clauses

Clause 1. A method comprising: obtaining image data representing a whole slide image (WSI) for medical testing or medical evaluation; determining, based at least in part on the image data, one or more algorithms to be assigned to the WSI based on a set of rules; executing the one or more algorithms to obtain one or more results associated with the WSI; and integrating the one or more results to generate a combined image; and displaying the combined image via a user interface of a digital pathology platform.

Clause 2. The method of clause 1, wherein the set of rules include at least one of a specimen type associated with the WSI, a stain type associated with the WSI, or a procedure code associated with the WSI.

Clause 3. The method of clause 1-2, wherein the one or more algorithms comprises at least two algorithms, the method further comprising executing the at least two algorithms in parallel.

Clause 4. The method of clause 3, wherein the at least two algorithms are executed on the same computing device.

Clause 5. The method of clause 1-4, wherein the one or more algorithms comprise a first algorithm and a second algorithm; and the executing the one or more algorithms further comprises: executing the first algorithm on a first computing device to obtain a first result; and executing the second algorithm on a second computing device to obtain a second result, the second computing device being different than the first computing device.

Clause 6. The method of clause 1-5, wherein the one or more results include at least one of biomarkers, cell segmentations, mitotic counts, or tissue boundaries and patterns.

Clause 7. The method of clause 1-6, wherein the one or more results comprise a first result and a second result; and the displaying the combined image further comprises: representing the first result in the combined image with a first line type; and representing the second result in the combined image with a second line type.

Clause 8. The method of clause 7, wherein the first result and the second result are presented in an overlapping manner.

Clause 9. The method of clause 7-8, further comprising: presenting a graphical element to selectively display the first result via the user interface of the digital pathology platform; receiving an indication of a selection of the graphical element; based at least in part on the indication, performing at least one of showing or hiding the first result in the combined image via the user interface of the digital pathology platform.

Clause 10. The method of clause 1-9, wherein the one or more results comprise a first result and a second result; and the displaying the combined image further comprises: representing the first result in the combined image with a first color; and representing the second result in the combined image with a second color.

Clause 11. An apparatus comprising: one or more processors; one or more non-transitory computer-readable media comprising computer-readable instructions that, when executed by one or more processors, cause the one or more processors to perform operations including: obtaining image data representing a whole slide image (WSI) for medical testing or medical evaluation; determining, based at least in part on the image data, one or more algorithms to be assigned to a whole slide image (the WSI) based on a set of rules; executing the one or more algorithms to obtain one or more results associated with the WSI; and integrating the one or more results to generate a combined image; and displaying the combined image via a user interface of a digital pathology platform.

Clause 12. The apparatus of clause 11, wherein the set of rules includes at least one of a specimen type associated with the WSI, a stain type associated with the WSI, or a procedure code associated with the WSI.

Clause 13. The apparatus of clause 11-12, wherein the one or more algorithms comprises at least two algorithms, the operations further comprising are executing the at least two algorithms in parallel.

Clause 14. The apparatus of clause 13, wherein the at least two algorithms are executed on the same computing device.

Clause 15. The apparatus of clause 14, wherein the one or more algorithms comprise a first algorithm and a second algorithm, the operations further comprising: executing the first algorithm on a first computing device; and executing the second algorithm on a second computing device that is different than the first computing device.

Clause 16. The apparatus of clause 14-15, wherein the one or more results include at least one of biomarkers, cell segmentations, mitotic counts, or tissue boundaries and patterns.

Clause 17. The apparatus of clause 16, wherein the one or more results comprise a first result and a second result; the operations further comprising: representing the first result in the combined image with a first line type; and representing the second result in the combined image with a second line type.

Clause 18. The apparatus of clause 17, wherein the first result and the second result are presented in an overlapping manner.

Clause 19. The apparatus of clause 17-18, wherein the one or more results comprise a first result and a second result; the operations further comprising: representing the first result in the combined image with a first color; and representing the second result in the combined image with a second color.

Clause 20. One or more non-transitory computer-readable media, stored thereon computer-readable instructions that, when executed by one or more processors, cause the one or more processors to perform acts comprising: obtaining image data representing a whole slide image (WSI) for medical testing or medical evaluation; determining, based at least in part on the image data, one or more algorithms to be assigned to the WSI based on a set of rules; executing the one or more algorithms to obtain one or more results associated with the WSI; and integrating the one or more results to generate a combined image; and displaying the combined image via a user interface of a digital pathology platform.

While the example clauses described above are described with respect to one particular implementation, it should be understood that, in the context of this document, the content of the example clauses can also be implemented via a method, device, system, computer-readable medium, and/or another implementation. Additionally, any of examples 1-20 may be implemented alone or in combination with any other one or more of the examples 1-20.

What is claimed is:

1. A method comprising:
   obtaining image data representing a whole slide image (WSI) for medical testing or medical evaluation;
   receiving a set of rules regarding how to assign which of multiple algorithms to the WSI based on a set of parameters comprising one or more of a specimen type associated with the WSI, a stain type associated with the WSI and a procedure code associated with the WSI;
   determining, based at least in part on the image data, one or more algorithms to be assigned to the WSI based on the set of rules;
   executing the one or more algorithms to obtain one or more results associated with the WSI; and
   integrating the one or more results to generate a combined image; and
   displaying the combined image via a user interface of a digital pathology platform.

2. The method of claim 1, wherein the one or more algorithms comprises at least two algorithms, and the method further comprises executing the at least two algorithms in parallel.

3. The method of claim 2, wherein the at least two algorithms are executed on a same computing device.

4. The method of claim 1, wherein the one or more algorithms comprise a first algorithm and a second algorithm; and executing the one or more algorithms further comprises:
   executing the first algorithm on a first computing device to obtain a first result; and
   executing the second algorithm on a second computing device to obtain a second result, the second computing device being different than the first computing device.

5. The method of claim 1, wherein the one or more results include at least one of biomarkers, cell segmentations, mitotic counts, or tissue boundaries and patterns.

6. The method of claim 1, wherein the one or more results comprise a first result and a second result; and displaying the combined image further comprises:
   representing the first result in the combined image with a first line type; and representing the second result in the combined image with a second line type.

7. The method of claim 6, wherein the first result and the second result are presented in an overlapping manner.

8. The method of claim 6, further comprising:
presenting a graphical element to selectively display the first result via the user interface of the digital pathology platform;
receiving an indication of a selection of the graphical element;
based at least in part on the indication, performing at least one of showing or hiding the first result in the combined image via the user interface of the digital pathology platform.

9. The method of claim 1, wherein the one or more results comprise a first result and a second result; and displaying the combined image further comprises:
representing the first result in the combined image with a first color; and
representing the second result in the combined image with a second color.

10. An apparatus comprising:
one or more processors;
one or more non-transitory computer-readable media comprising computer-readable instructions that, when executed by one or more processors, cause the one or more processors to perform operations including:
obtaining image data representing a whole slide image (WSI) for medical testing or medical evaluation;
receiving a set of rules regarding how to assign which of multiple algorithms to the WSI based on a set of parameters comprising one or more of a specimen type associated with the WSI, a stain type associated with the WSI and a procedure code associated with the WSI;
determining, based at least in part on the image data, one or more algorithms to be assigned to a whole slide image (the WSI) based on the set of rules;
executing the one or more algorithms to obtain one or more results associated with the WSI; and
integrating the one or more results to generate a combined image; and
displaying the combined image via a user interface of a digital pathology platform.

11. The apparatus of claim 10, wherein the one or more algorithms comprises at least two algorithms, and the operations further comprise executing the at least two algorithms in parallel.

12. The apparatus of claim 11, wherein the at least two algorithms are executed on a same computing device.

13. The apparatus of claim 12, wherein the one or more algorithms comprise a first algorithm and a second algorithm, and the operations further comprise:
executing the first algorithm on a first computing device; and
executing the second algorithm on a second computing device that is different than the first computing device.

14. The apparatus of claim 12, wherein the one or more results include at least one of biomarkers, cell segmentations, mitotic counts, or tissue boundaries and patterns.

15. The apparatus of claim 14, wherein the one or more results comprise a first result and a second result; and
the operations further comprise:
representing the first result in the combined image with a first line type; and
representing the second result in the combined image with a second line type.

16. The apparatus of claim 15, wherein the first result and the second result are presented in an overlapping manner.

17. The apparatus of claim 15, wherein the one or more results comprise a first result and a second result; and
the operations further comprise:
representing the first result in the combined image with a first color; and
representing the second result in the combined image with a second color.

18. One or more non-transitory computer-readable media, stored thereon computer-readable instructions that, when executed by one or more processors, cause the one or more processors to perform acts comprising:
obtaining image data representing a whole slide image (WSI) for medical testing or medical evaluation;
receiving a set of rules regarding how to assign which of multiple algorithms to the WSI based on a set of parameters comprising one or more of a specimen type associated with the WSI, a stain type associated with the WSI and a procedure code associated with the WSI;
determining, based at least in part on the image data, one or more algorithms to be assigned to the WSI based on the set of rules;
executing the one or more algorithms to obtain one or more results associated with the WSI; and
integrating the one or more results to generate a combined image; and
displaying the combined image via a user interface of a digital pathology platform.

* * * * *